United States Patent [19]

Svara

[11] Patent Number: 5,196,554

[45] Date of Patent: Mar. 23, 1993

[54] ALUMINUM BIS(HYDROXYMETHYL)PHOSPHINATE, AND A PROCESS FOR THE PREPARATION OF BIS(HYDROXYMETHYL)PHOSPHINATES

[75] Inventor: Jürgen Svara, Cologne, Fed. Rep. of Germany

[73] Assignee: Hoechst Aktiengesellschaft, Frankfurt am Main, Fed. Rep. of Germany

[21] Appl. No.: 695,470

[22] Filed: May 3, 1991

[30] Foreign Application Priority Data

May 19, 1990 [DE] Fed. Rep. of Germany ....... 4016258

[51] Int. Cl.$^5$ .................. C07F 9/28; C07F 9/02; C07F 5/06; C07F 3/06
[52] U.S. Cl. .................. 556/13; 556/20; 556/27; 556/130; 556/174; 556/182
[58] Field of Search .......... 556/13, 20, 27, 130, 556/174, 182, 15

[56] References Cited

U.S. PATENT DOCUMENTS 4,171,969 10/1979 Maier ....................... 71/86
4,180,495 12/1979 Sandler ................. 260/45.75 K

FOREIGN PATENT DOCUMENTS 2805074 8/1978 Fed. Rep. of Germany .
3616168 11/1987 Fed. Rep. of Germany .

OTHER PUBLICATIONS

Maier, "The Direct Synthesis of Hydromethylphosphinic Acid, Bis(hydroxymethyl)phosphonic Acid, and Methyl(hydroxymethyl)phosphinic Acid," Z. Anorg. allg. Chem., vol. 394, pp. 117–124 (1972).

*Primary Examiner*—José G. Dees
*Assistant Examiner*—Porfirio Nazario

[57] ABSTRACT

In a process for the preparation of bis(hydroxymethyl)-phosphinates of the formula $$M^{n+}[(HOCH_2)_2PO_2^-]_n$$

in which M is Li, Na, K, Ca, Mg, Zn or Al, and n is the valency of the element concerned and has a value of 1, 2 or 3, phosphinates of the formula $M^{n+}[H_2PO_2^-]_n$ are reacted with formaldehyde, trioxane or paraformaldehyde in water in an autoclave at a temperature of from 100° to 200° C. under the autogenous pressure at a residence time of from 5 to 20 hours. The novel chemical substance aluminum bis(hydroxymethyl)phosphinate of the formula $Al[(HOCH_2)_2PO_2^-]_3$ is also obtainable in this way.

2 Claims, No Drawings

ALUMINUM BIS(HYDROXYMETHYL)PHOSPHINATE, AND A PROCESS FOR THE PREPARATION OF BIS(HYDROXYMETHYL)PHOSPHINATES

The invention relates to a process for the preparation of bis(hydroxymethyl)phosphinates of the formula $$M^{n+}[(HOCH_2)_2PO_2^-]_n$$

in which M is Li, Na, K, Ca, Mg, Zn or Al, and n is the valency of the element concerned and has a value of 1, 2 or 3.

Bis(hydroxymethyl)phosphinates are used, for example, for the preparation of bis(aminomethyl)phosphinates, which can be used as active ingredients in herbicides and plant-growth regulators (cf. DE-28 05 074 A1). The calcium and magnesium salts of bis(hydroxymethyl)phosphinic acid can be employed as binders in basic refractory raw materials (cf. DE-36 16 168 A1).

According to DE-28 05 074 A1, bis(hydroxymethyl)phosphinic acid is prepared by reacting a 50% strength aqueous solution of phosphinic acid or sodium phosphinate with paraformaldehyde and concentrated hydrochloric acid under atmospheric pressure at the boiling point and at a residence time of 50 hours. In order to obtain about 5 kg of bis(hydroxymethyl)phosphinic acid, 35 liters of concentrated hydrochloric acid must be employed. The large excess of hydrochloric acid must be removed by evaporation during work-up.

It is known that formaldehyde forms bis(chloromethyl) ether and chloromethyl methyl ether in a hydrochloric acid medium. Care must be taken during the reaction and work-up that these highly carcinogenic compounds do not enter the environment. They must therefore be completely destroyed before work-up.

In DE-36 16 168 A1, the preparation of magnesium bis(hydroxymethyl)phosphinate or calcium bis(hydroxymethyl)phosphinate starts from the free phosphinic acid, and addition of other acids is avoided. However, the phosphinic acid is itself prepared from its salts by acidification and appropriate work-up (Ullmann's Encyklopädie der technischen Chemie [Ullmann's Encyclopedia of Industrial Chemistry], 4th Edition, Volume 18 (1979), pages 304–305).

Surprisingly, and this is the object of the invention, bis(hydroxymethyl)phosphinates have now been prepared while entirely avoiding acidic reaction conditions.

In detail, the process of the invention comprises reacting a phosphinate of the formula $M^{n+}[H_2PO_2^-]_n$ with formaldehyde, trioxane or paraformaldehyde in water in an autoclave at a temperature of from 100° to 200° C., preferably from 130° to 170° C., under autogenous pressure at a residence time of from 5 to 20 hours. In this way, aluminum bis(hydroxymethyl)phosphinate of the formula $$Al[(HOCH_2)_2PO_2^-]_3$$

can be obtained as a novel chemical substance.

EXAMPLE 1

60 g of sodium phosphinate monohydrate and 36 g of paraformaldehyde are dissolved in 70 ml of water, and the solution is heated to an internal temperature of 145°–150° C. with stirring in a Teflon-coated autoclave. The pressure increases to 7 bar during this operation. After 17 hours, the mixture is cooled, during which the pressure drops back to 1 bar. The clear, colorless solution obtained exhibits a content of 70 mol % of sodium bis(hydroxymethyl)phosphinate in the $^{31}$P-NMR spectrum. Evaporation on a rotary evaporator gives a colorless salt which solidifies in a glass-like manner. Melting point 103° C.
Elemental analysis (%): calc.: Na 15.53; P 20.920
found: Na 15.1; P 20.80

EXAMPLE 2

87.4 g of magnesium phosphinate hexahydrate, 42 g of paraformaldehyde and 96 g of water give, analogously to Example 1, after 18 hours at 145°–150° C., a colorless solution. The P-NMR spectrum exhibits 70 mol % of magnesium bis(hydroxymethyl)phosphinate. Evaporation leaves a colorless, crystalline salt. Melting point 116° C.
Elemental analysis (%): calc.: Mg 8.86; P 22.580
found: Mg 8.0; P 20.90

EXAMPLE 3

60 g of calcium phosphinate, 44 g of paraformaldehyde and 70 g of water give, analogously to Example 1, and according to the P-NMR spectrum, 83.5 mol % of calcium bis(hydroxymethyl)phosphinate, which, on evaporation, is obtained as a colorless, crystalline product. Melting point 278° C.
Elemental analysis (%): calc.: Ca 13.81; P 21.350
found: Ca 13.2; P 20.90

EXAMPLE 4

87.4 g of magnesium phosphinate hexahydrate and 113 g of 37% strength formaldehyde solution react analogously to Example 1 in 10 hours at 150° C. to give, according to the P-NMR spectrum, 77 mol % of magnesium bis(hydroxymethyl)phosphinate.

EXAMPLE 5

30 g of aluminum phosphinate, 24.3 g of paraformaldehyde and 80 g of water react analogously to Example 1 in 10 hours at 145°–150° C. to give a colorless crystal slurry, which is filtered off with suction and dried. The content of aluminum bis(hydroxymethyl)phosphinate is, according to the P-NMR spectrum, 95.9 mol % of the phosphorus-containing components determined. The substance decomposes without melting from about 340° C.

| X-ray powder diffractogram: | |
|---|---|
| d[Å] | $I/I_0$[%] |
| 8.4768 | 100.00 |
| 4.9038 | 2.55 |
| 4.5296 | 3.21 |
| 4.2891 | 3.10 |
| 4.0612 | 2.27 |
| 3.2091 | 6.55 |
| 2.8306 | 3.70 |
| 2.6918 | 3.91 |
| 2.4518 | 2.58 |
| 2.3585 | 4.68 |

We claim:
1. A process for the preparation of a bis(hydroxymethyl)phosphinate of the formula

$$M^{n+}[(HOCH_2)_2PO_2^-]_n$$

in which M is Li, Na, K, Ca, Mg, Zn or Al, and n is the valency of the element concerned and has a value of 1, 2 or 3, which comprises reacting a phosphinate of the formula $M^{n+}[H_2PO_2^-]_n$ with formaldehyde, trioxane or paraformaldehyde in water in an autoclave at a temperature of from 100° to 200° C. under the autogenous pressure at a residence time of from 5 to 20 hours.

2. The process claimed in claim 1, wherein the reaction is carried out at a temperature of from 130° to 170° C.

* * * * *